(12) United States Patent
Örning

(10) Patent No.: US 9,140,710 B2
(45) Date of Patent: Sep. 22, 2015

(54) TRANSCOBALAMIN II ASSAY METHOD

(75) Inventor: Lars Örning, Oslo (NO)

(73) Assignee: AXIS-SHIELD ASA, Oslo (NO)

( * ) Notice: Subject to any disclaimer, the term of this patent is extended or adjusted under 35 U.S.C. 154(b) by 623 days.

(21) Appl. No.: 12/289,291

(22) Filed: Oct. 24, 2008

(65) Prior Publication Data

US 2010/0099129 A1    Apr. 22, 2010

Related U.S. Application Data

(62) Division of application No. 10/474,506, filed as application No. PCT/GB02/01846 on Apr. 23, 2001, now Pat. No. 7,501,287.

(30) Foreign Application Priority Data

Apr. 23, 2001 (GB) .................................. 0109925.8

(51) Int. Cl.
| | |
|---|---|
| *G01N 33/82* | (2006.01) |
| *G01N 33/68* | (2006.01) |
| *G01N 33/543* | (2006.01) |
| *G01N 33/573* | (2006.01) |
| *C07K 16/18* | (2006.01) |
| *C07K 16/44* | (2006.01) |

(52) U.S. Cl.
CPC ............... *G01N 33/82* (2013.01); *C07K 16/18* (2013.01); *C07K 16/44* (2013.01); *G01N 33/543* (2013.01); *G01N 33/5735* (2013.01); *G01N 33/68* (2013.01); *C07K 2317/32* (2013.01)

(58) Field of Classification Search
None
See application file for complete search history.

(56) References Cited

U.S. PATENT DOCUMENTS

| | | | |
|---|---|---|---|
| 4,273,757 A |   | 6/1981 | Selhub et al. |
| 4,595,661 A |   | 6/1986 | Cragle et al. |
| 4,632,901 A | * | 12/1986 | Valkirs et al. ...................... 435/5 |
| 4,808,521 A |   | 2/1989 | Allen |
| 5,279,937 A | * | 1/1994 | Rowe ................................ 435/6 |
| 5,485,277 A | * | 1/1996 | Foster ............................ 356/445 |
| 5,688,504 A |   | 11/1997 | Morgan, Jr. |
| 5,846,837 A | * | 12/1998 | Thym et al. .................... 436/170 |
| 6,221,625 B1 | * | 4/2001 | Ashihara et al. ............... 435/7.9 |
| 6,478,938 B1 | * | 11/2002 | Paek et al. ................. 204/403.01 |
| 6,939,678 B1 | * | 9/2005 | Buechler et al. ............... 435/7.1 |

FOREIGN PATENT DOCUMENTS

| | | | | |
|---|---|---|---|---|
| EP | 0 310 132 A2 |   | 4/1989 |   |
| WO | WO 00/17659 | * | 9/1999 | ............. G01N 33/82 |

OTHER PUBLICATIONS

Afman et al. "Reduced vitamin B12 binding by transcobalamin II increases the risk of neural tube defects" QJM (Mar. 2001) 94 (3): 159-166.*

Harlow, E. and Lane, D., Antibodies: A Laboratory Manual (1988) Cold Spring Harbor Laboratory Press, Cold Spring Harbor, NY, pp. 578-582.*

Orning et al., "Characterization of a monoclonal antibody with specificity for holo-transcobalamin", Nutrition & Metabolism, BioMed Central, Jan. 2006, vol. 3, No. 3, pp. 1-11.

Nomura et al., "Three-Site Sandwich Radioimmunoassay with Monoclonal Antibodies for a Sensitive Determination of Human Alpha-Fetoprotein", Journal of Immunological Methods, 1983, vol. 58, pp. 293-300.

Nexo et al., "Measurement of Transcobalamin by ELISA", Clinical Chemistry, 2000, vol. 46, No. 10, pp. 1643-1659.

Ulleland et al., "Direct Assay for Cobalamin Bound to Transcobalamin (Holo-Transcobalamin) in Serum", Clinical Chemistry, 2002, vol. 48, No. 3, pp. 526-532.

Wickramasinghe et al., "Limited value of serum holo-transcobalamin II measurements in the differential diagnosis of macrocytosis", J. Clin. Pathol. 1996, vol. 49, pp. 755-758.

* cited by examiner

*Primary Examiner* — Christine Foster
(74) *Attorney, Agent, or Firm* — Bacon & Thomas, PLLC

(57) ABSTRACT

An assay method for determining transcobalamin saturation wherein a transcobalamin containing liquid sample is contacted with a porous substrate with immobilized thereon a transcobalamin immobilizing ligand and with a reporter-labelled transcobalamin binding partner and wherein signals from reporter labels which become immobilized on said substrate are detected, characterized in that one of said ligand or said binding partner comprises a first ligand or binding partner capable of specific binding to holo transcobalamin and a second ligand or binding partner capable of binding to apo transcobalamin or to holo and apo transcobalamin.

15 Claims, 1 Drawing Sheet

TRANSCOBALAMIN II ASSAY METHOD

CROSS REFERENCES TO THE RELATED APPLICATIONS

This application is a divisional application of U.S. patent application Ser. No. 10/474,506, filed Mar. 4, 2004, now U.S. Pat. No. 7,501,287 B2 (of which the entire disclosure of the pending, prior application is hereby incorporated by reference).

FIELD

The invention relates to improvements in and relating to diagnostic assay methods, in particular assays for transcobalamin.

BACKGROUND

Cobalamin or vitamin $B_{12}$ is a water-soluble vitamin which forms part of the vitamin B complex found in foods. The core molecule consists of a corrin ring of four pyrole units which surround the essential cobalt atom. Cobalamin is the only vitamin which cannot be synthesised by animals or plants and must be absorbed from food in the gut. It can however be stored in the liver. It is synthesised by micro-organisms, in particular by anaerobic bacteria and yeasts.

Cobalamin functions in vivo as a co-enzyme and cobalamin enzymes catalyse three types of reaction: (i) intra-molecular rearrangements, for example, the formation of succinyl CoA from L-methylmalonyl CoA; (ii) methylations, for example, the formation of methionine by methylation of homocysteine; and (iii) reduction of ribonucleotides to deoxyribonucleotides in some micro-organisms. In mammals, only two enzymic reactions, those specifically mentioned in (i) and (ii) above, are known to require cobalamin as a co-enzyme.

In the process of digestion, a salivary protein called haptocorrin, hereinafter referred to as HC (which is also referred to in the art as R-binder or transcobalamins I and III collectively), binds cobalamin in the upper gastrointestinal tract forming a complex which passes through the stomach. Pancreatic enzymes digest the cobalamin-haptocorrin (holo-HC) complex in the ileum, liberating cobalamin which is then bound to a protein called intrinsic factor, which is secreted by the gastric mucosa, to form a further complex. The cobalamin-intrinsic factor complex binds to a specific receptor in the lining of the terminal ileum, whereupon it is dissociated by a releasing factor and the cobalamin transported actively across the membrane of the ileum into the blood stream.

Cobalamin does not circulate in the body in a free form in an appreciable amount. Probably 99% or so of cobalamin is bound by haptocorrin, transcobalamin or albumin.

The protein believed to be responsible for transporting cobalamin to target tissues is transcobalamin II (hereinafter simply referred to as transcobalamin or TC), a critical trace protein without which cobalamin cannot cross cell membranes. Despite this important metabolic function, only about 6-25% of cobalamin in the serum is bound to TC and most is carried by HC. TC is a single chain polypeptide of 45 kDa found primarily in serum, seminal fluid and cerebro-spinal fluid. Cobalamin bound TC or holo-TC, attaches to specific receptors on cell membranes and once bound, the holo-TC complex is taken into cells by pinocytosis.

TC is synthesised by the liver, vascular endothelium, enterocytes, macrophages and fibroblasts and circulates predominantly as apo-TC, i.e. lacking bound cobalamin. It has a short half life of approximately 90 minutes.

Less than a quarter of the total plasma cobalamin is associated with TC. The rest is bound to HC or albumin as mentioned above. Since cobalamin must be absorbed from food, any conditions which result in impaired gastric function, for example, gastroenteritis or conditions resulting in gastric atrophy, or an inability to produce functional haptocorrin, intrinsic factor, releasing factor, TC or TC receptors, can result in impaired uptake of cobalamin and resultant deficiency.

Certain population sub-groups, for example the aged, pregnant women, patients with chronic or acute gastrointestinal disease, those suffering from certain autoimmune diseases, those with a family history of pernicious anaemia and AIDS sufferers, are particularly prone to cobalamin deficiency.

The clinical manifestations of cobalamin deficiency are varied and numerous but primarily involve anaemia, megaloblastic haematopoiesis and functional and structural disorders of the nervous system. Around 60% of individuals diagnosed as being deficient in cobalamin are anaemic, but in many neurological symptoms are the only clinical signs observed. Around 10% of patients exhibit psychiatric symptoms and around 40% exhibit both neurological and psychiatric symptoms.

Early diagnosis of cobalamin deficiency is crucial to ensure a good prognosis for patients, since some of the manifestations of cobalamin deficiency, particularly the neuropsychiatric effects, are irreversible if not detected and alleviated by cobalamin therapy quickly.

It is desirable therefore to accurately assess the cobalamin level of an individual in an expedient and efficient manner, with a view to establishing whether or not the individual may be suffering from cobalamin deficiency.

Measurement of total plasma cobalamin, i.e. cobalamin (and cobalamin like substances) bound to HC or TC, has been used in attempts to assess cobalamin deficiency. This technique results in a broad based concentration distribution within a population which is considered to be normal and hence produces a wide reference range. Within individuals however, the range of available cobalamin considered to be normal for that individual, is very narrow. It has been observed that although an individual's metabolically active cobalamin concentration has moved outside their own reference range, their total plasma cobalamin content remains within the range considered to be normal for the population. Under such circumstances, cobalamin deficiency can go undetected. Such an unreliable method is clearly undesirable and it is well recognised that such serum or plasma cobalamin measurements have low diagnostic sensitivity and specificity.

Microbial assays involving micro-organisms dependent upon cobalamin for growth, have been developed and used in measuring plasma cobalamin concentration, but in addition to the difficulty of estimating the appropriate reference range, these methods require extraction and conversion of the cobalamins which is very time consuming, troublesome and wholly unsuited for rapid laboratory screening.

Alternative methods for assessing cobalamin deficiency involve measuring the accumulation of metabolites in the plasma which require cobalamin for their conversion. Plasma methylmalonate and plasma homocysteine levels increase in cobalamin deficient individuals and make good candidate molecules for correlation with vitamin $B_{12}$ deficiency. Methods based on homocysteine assessment have been shown, however, to be complicated, impractical and show poor specificity and sensitivity. Whilst methods based on methylmalonate measurement are accurate and reliable, they are cumbersome and require analysis by combined gas-chromatography/mass-spectrometry and are hence expensive and again unsuitable for routine clinical screening.

It has also been suggested that measurement of TC bound cobalamin as opposed to total plasma cobalamin may provide a reliable clinical indictor of the likelihood of cobalamin deficiency (Herbert et al. (1990) Am. J. Hematol. 34:132-139; Wickramasinghe and Fida (1993) J. Clin. Pathol. 46:537-539; U.S. Pat. No. 4,680,273). Such efforts to determine holo-TC concentration were mostly indirect, estimating holo-TC concentration as the difference between total plasma cobalamin and the cobalamin concentration of TC depleted plasma.

Such TC depletion may be accomplished by adsorption to ammonium sulphate (Carmel (1974) Am. J. Clin. Pathol. 62:367-372), microsilica (Herzlich & Hubert (1988) Lab. Invest. 58:332-337; Wickramasinghe & Fida (1993) J. Clin. Pathol. 46:537-539), microfine glass (Vu et al. (1993) Am. J. Hematol. 42:202-211) or immobilized anti-TC polyclonal antibodies (Lindemans et al. (1983) Clin. Chim. Acta 132:53-61). The concentration of cobalamin in total plasma and the depleted fraction is performed by methods well known in the art such as radio or enzyme immunoassay techniques. These methods are unsuitable for routine screening whether automated or not automated because they are complex and time consuming and because the low degree of specificity of the adsorptive materials used results in insufficient separation of holo-TC and holo-HC resulting in an overestimation of holo-TC. Lot-to-lot variation of the adsorptive material introduces further errors and most importantly, the subtraction of one large volume from another large volume results in unacceptable inaccuracies and unreliability.

Other attempts to assess TC have involved separating TC from other serum components, including HC, using its lipophilicity. Thus Kapel et al. (1988) Clin. Chim. Acta 172:297-310, Benhayoun et al. (1993) Acta Haematol. 89:195-199 and Toft et al. (1994) Scand. J. Clin. Lab. Invest. 54:62 disclose methods for separating TC from HC using heparin sepharose, silica gel or cellulose respectively. These methods however suffer from the same disadvantages as the indirect methods since they rely on the same adsorptive materials. Also, the low plasma concentration of holo-TC renders these methods unsuitable for combination with existing methods of cobalamin quantification. The normal range of holo-TC is 35-160 pM and values below 35 pM would generally be considered as indicative of cobalamin deficiency. The reported analytical sensitivity of most routine methods for plasma cobalamin is about 40 pM but in practice it is often much higher, typically around 90 pM. Hence, normal plasma levels of holo-TC are below or near the sensitivity limit of the routine methods for cobalamin quantification.

Possibly the most accurate method currently recognised for determining TC bound cobalamin involves adsorbing TC to silica and then assaying the bound fraction for cobalamin content using either an immunoassay as described for example by Kuemmerle et al. (1992) Clin. Chem. 38/10: 2073-2077, or a microbiological assay, the latter apparently producing the best results. This method requires an entire working day to perform only twenty assays. It is very expensive and impractical and poorly suited to routine clinical diagnostic laboratory investigations.

In WO 00/17659, an alternative method for determining holo-TC concentration in which, for example, a cell-free sample is contacted with an antibody specific for TC immobilized on magnetizable particles and with a non-overlapping, non-immobilized, radiolabelled antibody specific for holo-TC. The particles are separated out using a magnetic field and washed and their radioactivity is measured so providing a measurement of the holo-TC content of the sample. This method however requires calibration and is more suited for performance in a clinical laboratory than by a physician or physician's assistant at the point of care for the patient.

There thus still exists a need for an assay for holo-TC which is simple and operable at the point of care.

SUMMARY

We have recognized that such a simple assay can be achieved by measuring not holo-TC content but TC saturation, i.e. the proportion of TC that is in the holo form, by using two labelled specific binding partners, one for holo-TC and the other for apo-TC or for both holo and apo-TC and by determining the ratio of the signals from the two labels. Moreover such an assay is volume independent, i.e. the quantity of the liquid sample (e.g. body fluid) used need not be precisely determined. This is a major advantage for point-of-care use.

DESCRIPTION

Thus viewed from one aspect the invention provides an assay method for determining transcobalamin saturation wherein a transcobalamin containing liquid sample is contacted with a porous substrate with immobilized thereon a transcobalamin immobilizing ligand and with a reporter-labelled transcobalamin binding partner and wherein signals from reporter labels which become immobilized on said substrate are detected, characterised in that one of said ligand or said binding partner comprises a first ligand or binding partner capable of specific binding to holo transcobalamin and a second ligand or binding partner capable of binding to apo transcobalamin or to holo and apo transcobalamin.

In one embodiment, the assay method of the invention comprises:
(i) contacting a transcobalamin containing liquid sample with a porous substrate having immobilized thereon a transcobalamin-immobilizing ligand;
(ii) before, during or after step (i) above, contacting transcobalamin of said sample with a first and a second reporter-labelled binding partner for transcobalamin, said first binding partner being capable of binding both holo and apo transcobalamin or being a specific binding partner for apo transcobalamin and said second binding partner being a specific binding partner for holo transcobalamin; and
(iii) detecting signals from the reporter labels of said binding partners immobilized on said substrate and determining therefrom an indication of transcobalamin saturation in said sample.

Alternatively, the substrate may have a first region having immobilized thereon a ligand which is a specific binding partner for holo transcobalamin and a second region having immobilized thereon a ligand which is a specific binding partner for apo transcobalamin or which is capable of immobilizing both holo- and apo transcobalamin and step (iii) may comprise detecting signals from said first and second regions.

By a specific binding partner or ligand is meant one which binds to TC (ie. apo-TC and/or holo-TC as required) by virtue of its specific chemical structure or conformation and not simply by virtue of an overall physico-chemical property (such as lipophilicity) which may be common to many components of a body fluid sample. The specific binding partner or ligand will generally be either an antibody, an antibody fragment, a single chain antibody, an antibody fragment dimer, trimer or tetramer, or a compound with an affinity for apo-TC and/or holo-TC, such as a cell surface receptor, a polypeptide, an oligopeptide, an oligonucleotide, a small organic chemical, etc. Other specific binding partners or ligands may be selected from a combinatorial chemistry or phage display library or specific binding sequences of DNA or RNA.

If the specific binding partner or ligand is an antibody it may be polyclonal but will preferably be monoclonal. Monoclonal antibodies can be generated with much greater specificity and uniformity than polyclonal antibodies and this reduces cross-reactivity with other components of the body fluid, in particular HC and where appropriate, the alternative conformation, e.g. the apo form of the target analyte. The uniformity and reproducibility offered by monoclonal antibodies relative to polyclonal antibodies ensures a greater accuracy which is vital for an assay wherein the analyte is in such low concentration. Alternatively, it may be an antibody fragment for example F(ab), F(ab')$_2$ or F(v) fragment. The antibodies or antibody fragments may be monovalent or divalent and may be produced by hybridoma technology or be of synthetic origin, and generated by recombinant DNA technology or chemical synthesis. Single chain antibodies or other antibody derivatives or mimics could for example be used. The antibody may be directed or raised against any epitope, component or structure of the apo and/or holo-TC protein as appropriate.

The specific binding partner or ligand (sbp) for holo-TC used in the assay method of the invention should have a specificity for holo-TC (as opposed to apo-TC) which is at least 10-fold, preferably at least 50-fold, more preferably at least 100-fold, i.e. in an excess of apo at least 10 times as much of the holo-TC sbp should bind to holo-TC than to apo-TC. In general therefore it will be preferred to select the holo-TC sbp using in vitro methods, rather than by antibody generation in a host animal. Accordingly screening for candidate holo-TC sbps will preferably be done using in vitro libraries, e.g. phage display antibody (especially single chain antibody) libraries or oligonucleotide or chemical libraries. The affinity of the holo-TC sbp for holo-TC will moreover preferably be such that nanomolar concentrations of holo-TC can be detected.

Candidate holo-TC sbps can for example be selected by immobilizing holo-TC on a substrate (e.g. beads or sheets), e.g. by amide coupling, and panning the library in the presence of an excess of non-immobilized apo-TC. The substrate should then be washed thoroughly and holo-TC binding candidates should then be released and identified by the means conventional for the library type.

Candidates may then be tested for cross-reactivity for apo-TC and candidates having sufficient preference for holo-TC rather than apo-TC can then be selected. Desirably candidate holo-TC sbps will also be screened to deselect sbps which are cross-reactive for HC.

Most preferably, the binding regions of the holo-TC sbps should be non-peptidic, e.g. they may be small organic molecules or oligonucleotides (e.g. 20 to 50-mers).

Candidate apo-TC sbps can be selected in equivalent fashion; however it will generally be preferred to use a holo-TC sbp and a non-overlapping TC sbp (i.e. one which binds to both apo and holo TC) and TC sbps are well known from the literature (see for example Quadros et al., Biochem. Biophys. Res. Commun. 222: 149-154 (1996) and McLean et al., Blood 89: 235-242 (1997)).

Once candidate holo TC sbps and TC or apo-TC sbps have been selected, they may be reporter-labelled by conventional means.

The reporters may be the same if different ligands are immobilized on different regions of the substrate; however otherwise the reporters used should be different, i.e. their signals should be interdistinguishable.

The reporter moieties in the sbps may be any of the conventional reporters, e.g. radiation emitters or absorbers, in particular electromagnetic radiation emitters or absorbers, enzymes, or, less preferably, radiolabels, etc. In the case of enzymatic reporter moieties, the signals detected will be signals, e.g. emitted light, from the reaction catalysed by the enzyme. Thus the detected signals may be generated directly or indirectly by the reporter moieties.

By means of example only, some suitable examples of coloured or fluorescent compounds which may be used to label a sbp detectably in the present invention are anthraquinones, azo dyes, azine dyes such as oxazines and thiazines, triazines, naturally occurring pigments such as porphyrins, phycobiliproteins, including phycoerythins and phycoquanins, chlorophylls and their analogues and derivatives, carotenoids, acrinidines, xanthenes including fluoresceins and rhodamines, indigo-dyes, thioxanthenes, coumarins, polymethines including di and tri arylmethines and derivatives thereof of phthalocyanines and metal phthalocyanines.

Similarly, a wide range of radioactive compounds may be used as the signal forming label, among them Iodine-125-labelled compounds.

Alternatively, the sbp may be conjugated to natural or synthetic compounds which can produce a chemiluminescent signal which may be assayed in known manner (Cormier, M. J. et al.; Chemiluminescence and Bioluminescence, Plenum Press, New York 1973). Suitable chemiluminescent compounds include luciferin, oxalic esters, 1,2-dioxethane, luminol or derivatives thereof, but are not limited to these. If appropriate, hydrogen peroxide, enzymes e.g. luciferase, alkaline phosphatase or other chemicals may be used to produce the chemiluminescent signal from the signal-producing molecules used.

Preferably, the sbp is conjugated to a polymeric "scaffold" which carries a plurality of reporter moieties, e.g. enzymes, chromophores, fluorophores, etc. In this way the signal may be magnified, e.g. several hundred-fold. Typical polymer scaffolds include dextran (e.g. Amdex), polyethylene glycol and dendrimers (e.g. starburst dendrimers).

Strongly-anionic signal forming molecules may not be preferred for use in the method of the invention, since they have a tendency to bind to serum proteins such as human serum albumin (HSA) which may be present in the sample. Particularly suitable examples which may be used are fluorescein isothiocyanate, Rhodamine B or N-(resorufin-4-carbonyl)piperidine-4-carboxylic acid-N-hydroxysuccinimide-ester) (resos).

Where the reporter is a light emitter or absorber, it is particularly preferred (especially for the labelled holo-TC sbp) that the reporter comprise a plurality of chromophores or fluorophores so that the signal is magnified. One particularly preferred group of reporters is the group of reporters capable of time-delayed fluorescence, another is the group capable of provoking luminescence. Specific examples of reporters include β-galactosidase and chicken alkaline phosphatase.

It is well known in the art to immobilise affinity molecules, e.g. antibodies and antibody fragments for separation purposes, for example by binding or coupling the ligands, optionally by means of a linker, to any of the well known solid supports or matrices which are currently widely used or proposed for separation or immobilisation, and any known method in the art could be used. Such solid phases may take the form of particles, sheets, gels, filters, membranes, fibres or capillaries. Techniques for binding the ligand to the porous substrate are thus extremely well known and widely described in the literature.

In the method of the invention, the substrate is preferably a porous sheet or strip (e.g. of a cellulosic material, preferably nitrocellulose), especially preferably mounted on a non-porous support, optionally with an absorbent backing which serves to promote absorption of the liquid sample into the substrate by capillary action. Thus in one preferred embodiment the substrate layer, preferably backed by an absorbent layer, is mounted on a dipstick. In another preferred embodiment the substrate layer preferably backed by an absorbent layer, is held in a plastic casing provided with an aperture for application of the liquid sample to the exposed surface of the substrate layer and for reading the signals from the substrate layer.

Signal generation, if required, may be by whatever means are suitable for the selected labels, e.g. by exposure to light or to a substrate for an enzymatic label, and signal detection may be by any detector suitable for detecting the emitted signals, e.g. radioactivity or light detectors. Especially preferably, where the signals are light signals, a digital camera will be used as the detector, if necessary provided with a filter, prism or other means to ensure that the desired wavelength band is allowed to reach the detector.

Detection of the signals from the two labelled sbps may be simultaneous or sequential. Simultaneous detection is preferred.

Detected signal manipulation to generate a quantitative, semi-quantitative or qualitative indication of TC saturation is conveniently performed by a computer, preferably one built into the apparatus used to perform the assay and arranged to control performance of the assay. Where the signal forming labels are different in the sbps, the assay will require calibration in conventional fashion to transform the signal ratio (Sa/Sb or Sa/(Sa+Sb) where Sa is the holo-TC sbp signal and Sb is the TC or apo-TC sbp signal respectively) into a TC saturation value. Accordingly the assay may if desired be provided with calibration standards containing apo and holo-TC in known ratios.

In an alternative embodiment, any method of the current invention may be carried out on the surface of a chip-type substrate within a surface plasmon resonance (SPR) detector. In such a method, the need for active labelling of the specific ligands or substrates is avoided and binding is detected directly by the additional mass of the specific binding ligands or specific binding partners binding to the surface. In a preferred example of this alternative, a TCII binder is immobilised on the surface of an SPR "chip" (e.g. by gold-coating of the chip, followed by absorption of a thiol-conjugated TCII binder or by amide coupling of the binder to a dextran-coated chip). The chip is then placed in the surface plasmon resonance detector and a solution containing the sample is caused to flow over the chip, so binding holo-TC and apo-TC from the sample onto the immobilised ligand. A solution containing a first specific binder with specificity for apo-TC or for both apo-TC and holo-TC is then caused to flow over the chip and the binding measured by surface plasmon resonance to give a first signal. This first specific binder is then optionally washed off and a second specific binder with specificity for holo-TC only is passed over the chip. A second signal, representing the binding to holo-TC is detected by surface plasmon resonance. This difference between the first and second SPR is then used to calculate the TCII saturation. By using SPR, any ligands or specific binding partners described as "labelled" or "reporter labelled" may be detected by mass without any additional or active label. In this case the "label" is simply the mass of the specific binding partner or ligand.

The sample applied to the substrate is preferably a body fluid or tissue-derived liquid, preferably a cell-free liquid, especially plasma or serum from a mammalian, especially human, subject.

Viewed from a further aspect the invention provides an assay kit comprising:
 a porous substrate having immobilized thereon a TC-immobilizing ligand;
 a first and a second reporter-labelled binding partner for transcobalamin, said first binding partner being capable of binding both holo and apo transcobalamin or being a specific binding partner for apo transcobalamin and said second binding partner being a specific binding partner for holo transcobalamin;
 optionally, a washing agent;
 optionally, a substrate for an enzymatic reporter label;
 optionally, at least one calibration standard containing apo and holo-TC at known ratio; and
 optionally, a detector capable of detecting signals from said reporter labels.

In an alternative format, the transcobalamin saturation can be determined by binding to different regions of the substrate two ligands, a first which immobilizes holo-TC and a second which immobilizes apo-TC (or apo and holo-TC), and contacting the substrate with the TC-containing sample and a reporter labelled sbp for TC. In this form, which forms a further aspect of the invention, the signals are read from the different regions of the substrate and the signal ratio Sa/(Sa+Sb) or Sa/Sb (where Sa is the signal for the holo-TC ligand region and Sb is the signal for the apo-TC or holo and apo-TC ligand region) is indicative of the TC saturation level. The "regions" of the substrate in this or other aspects of the invention may for example be different areas of the surface of a membrane, different membrane surfaces on a dipstick, different membranes in a casing, or different sets of separable beads (e.g. one set being magnetizable, the other not).

In this format, the assay method of the invention typically comprises:
 (i) contacting a transcobalamin containing liquid sample with a porous substrate having immobilized thereon in different regions thereof a first and a second transcobalamin-immobilizing ligand, said first ligand being capable of specific binding to holo transcobalamin and said second ligand being capable of immobilizing apo or apo and holo transcobalamin;
 (ii) before, during or after step (i), contacting transcobalamin of said sample with a reporter-labelled binding partner for transcobalamin; and
 (iii) detecting signals from the reporter labels of said binding partner immobilized on the different regions of said substrate and determining therefrom an indication of transcobalamin saturation in said sample.

Viewed from a yet further aspect the invention thus provides an assay kit comprising:
 a porous substrate having immobilized thereon in different regions thereof a first and a second transcobalamin-immobilizing ligand, said first ligand being capable of specific binding to holo transcobalamin and said second ligand being capable of immobilizing apo or apo and holo transcobalamin;
 a reporter-labelled binding partner for transcobalamin;
 optionally, a washing agent;
 optionally, a substrate for an enzymatic reporter label;
 optionally, at least one calibration standard containing apo and holo-TC at known ratio; and optionally, a detector capable of detecting signals from said reporter labels.

The invention will now be described further with reference to the following non-limiting Examples and to the drawings in which;

BRIEF DESCRIPTION OF THE DRAWINGS

In FIG. 1, "label-spb1" represents a first specific binding partner having a first label attached and "sbp-label2" represents a second specific binding partner having a second label attached. It can be seen that the signal from label1 corresponds to the holo-TC level and the signal from label2 corresponds to the total apo- and holo-TC levels.

In FIG. 2, it can be seen that holo-TCII has bound to the first (left hand) region and apo-TCII to the second (right hand) region. The "sbp-label" represents a specific binding partner for TC having an attached label. In this way, the signals from the two regions represent the holoTC and apoTC content respectively.

In FIG. 3, a chip surface has been modified by attachment of a first monoclonal antibody (mAb1). This binds to apoTC and to holoTC from a sample. The second antibody (mAb2) also binds either holo-TC or apo-TC, thus giving an SPR signal for total TC content when this is added. The third antibody (mAb3) binds only to holo-TC and so gives an SPR signal representing the holo-TC content.

EXAMPLES

Example 1

Generation of Holo-TC Sbp

A) Immobilization of Holo-TC on Beads

Figure 1:
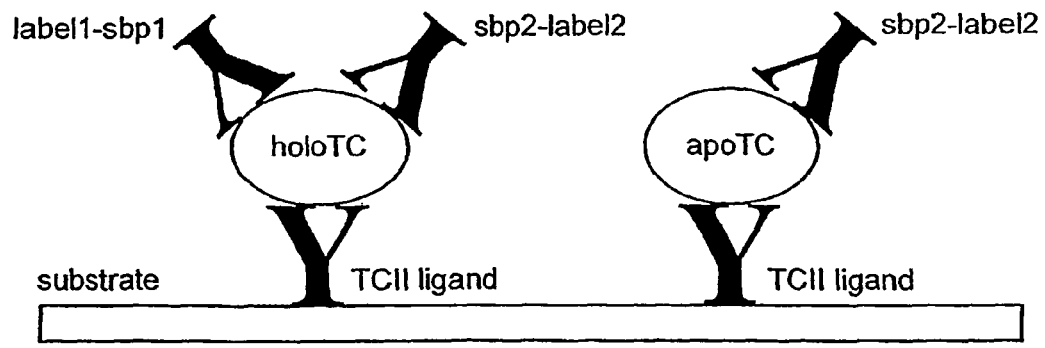
FIG. 1 represents a substrate upon which TC ligands have been immobilised.
Figure 2:
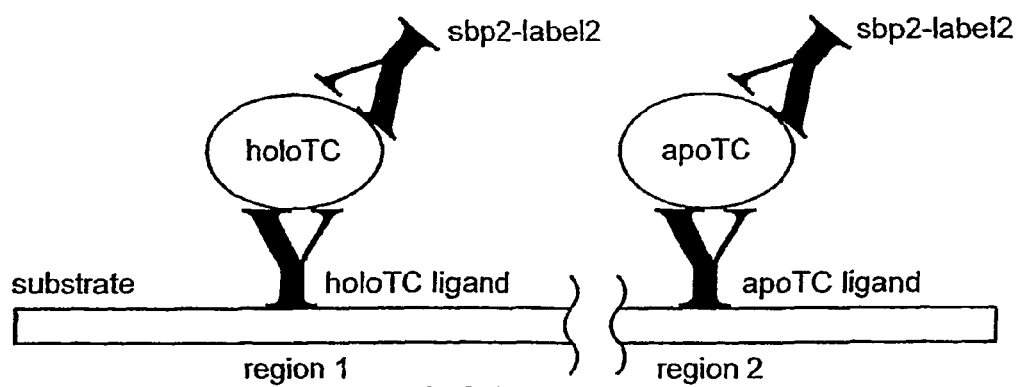
FIG. 2 represents a substrate having two regions, one containing immobilised ligands specific to holo-TCII and a second having immobilised ligands specific to apo-TCII.
Figure 3:
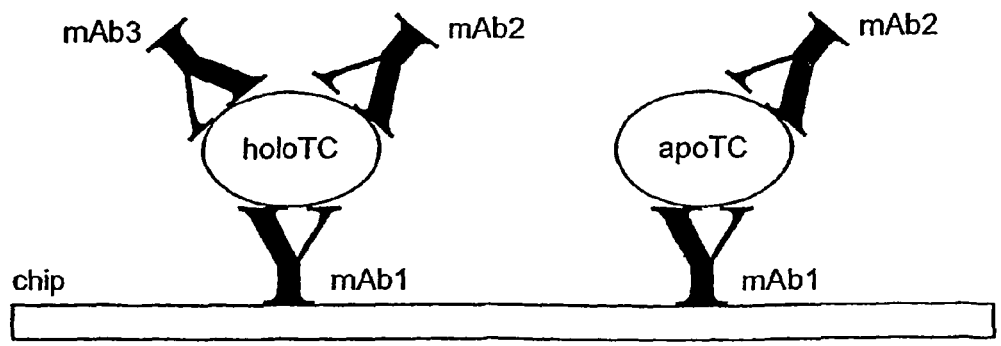
FIG. 3 represents a chip within a surface plasmon resonance detector having antibodies for TC immobilised on the surface.

One milliliter of 0.2M 1-ethyl-3-(3-dimethylamino-propyl)-carbodiimide (EDAC) in 0.1M 2-(N-morpholine)-ethanesulfonic acid (MES), pH 5.0 is mixed with 1.0 mL 2% (w/v) carboxylate-modified beads (1 μm diameter Merck-Estapor) in 0.1M MES, pH 5.0. The mixture is treated with bath sonication to disperse the reagents and is then rotated end-over-end for 1 h at room temperature. The mixture is centrifuged at 300 g and the pellet is washed with 0.1 M MES, pH 7.0, centrifuged and is resuspended in 1.0 mL deionized water. The EDAC activated beads are mixed in a small plastic vial with the same volume of 1 mg/mL holo-TC in 0.1M 3-[N-morpholino]-propane sulphonic acid (MOPS), pH 7.5 and rotated overnight at room temperature. Thereafter, the mixture is washed twice with 0.05% TWEEN® 20 (aq) and twice with 50 mM Tris buffer, pH 7.4, containing 5 mg/mL BSA. The coated beads having a monolayer of holo-TC of about 10 μg/mg are stored at 0.1% in 50 mM Tris, pH 7.4, 0.15M NaCl, and 1 mg/mL BSA.

B) (i) Biopanning of Aptamer Libraries with Holo-TC as the Target Molecule

A library of double-stranded DNA sequences is prepared by a mixture of chemical and enzymatic steps. Typically, $10^{14}$-$10^{15}$ single stranded DNA (ssDNA) sequences of length 40 nucleotides are made synthetically and are then converted to the double-stranded form by enzymatic means prior to PCR amplification. Second, the double-stranded DNA is transcribed to yield a library of single-stranded RNA or modified RNA. Third, the RNA library is challenged with the intended target molecule. The selected molecules are reverse transcribed and then amplified by PCR (for DNA libraries PCR is sufficient). The subset of sequences that bind to the target becomes the pool for a second round of biopanning. Usually the selection process takes from 7 to 15 rounds.

Five nmol of gel-purified, synthetic template DNA containing 40 nucleotides contiguous sequence flanked by defined primer annealing sequences SEQ ID NO. 1 [5'-GG-GAGGACGATGCGG-(N)$_{40}$—CAGACGACTCGCCCGA-3'] is amplified by four PCR cycles with primers SEQ ID NO. 2 5'-TAATACGACTCACTATAGGGAGGACGATGCGG-3' and SEQ ID NO. 3 5'-TCGGGCGAGTCGTCTG-3'. Approximately 800 pmol of the PCR-derived template DNA (about $5\times10^{14}$ molecules) are transcribed in vitro by T7 RNA polymerase (1000 U) in a 3 mL transcription reaction consisting of 40 mM TrisHCl (pH 8.0), 12 mM MgCl$_2$, 1 mM Spermidine, 5 mM dithiothreitol (DTT), 0.002% Triton X-100 (v/v), 4% polyethylene glycol (w/v) and 2 mM each of ATP, guanidine-5'-triphosphate (GTP), 2'-NH$_2$CTP and 2'-NH$_2$UTP (CTP=cytidine 5'-triphosphate and UTP=uridine 5'-triphosphate). Full length transcription products are purified on 8% polyacrylamide gels under denaturing conditions, suspended in binding buffer (10 mM TrisHCl, 0.1 mM EDTA, 2.5 mM MgCl$_2$, pH 6.8), heated to 70° C. and chilled on ice.

The RNA pool is incubated at 37° C. for 15 min with about 10 μg holo-TC immobilized on beads and 100 μg of apo-TC free in the solution as competitor. The beads are separated by means of centrifugation and are immediately washed with 5 mL binding buffer. Bound RNA molecules are eluted from the beads by lowering the pH, recovered by ethanol precipitation and reverse transcribed by avian myeloblastosis virus transcriptase (Life Sciences) at 48° C. for 45 min with the DNA sequence SEQ ID NO. 3 5'-TCGGGC-GAGTCGTCTG-3' as the primer. Following PCR amplification of the cDNA, the resulting duplex DNA template is transcribed in vitro to obtain RNA for the next round of selection. The amount of holo-TC coated beads in the binding reaction are successively reduced to progressively increase the selection pressure. The selection process is repeated until the affinity of the enriched RNA pool for holo-TC is substantially increased. At this point, cDNA is amplified by PCR with primers SEQ ID NO. 4 5'-CCGAAGCTTA-ATACGACTCACTATAGGGAGGACGATGCGG-3' and SEQ ID NO. 5 5'-GCC GGATCCTCGGGCGAGTCGTCTG-3', which introduces BamHI and HindIII restriction sites (underlined) at the 5' and 3'-ends of the PCR products, respectively. The PCR products are digested with BamHI and HindIII and cloned into pUC18 that has been digested with the same enzymes and introduced into *Escherichia coli* SURE (Stratagene) by electroporation. Plasmids are isolated from single bacterial clones and are screened and sequenced using standard techniques as described in e.g. Sambrook et al. (1989) Molecular Cloning: A Laboratory Manual, 2nd edition Cold Spring Harbor Laboratory Press, Cold Spring Harbor, N.Y., pp C1.

In order to confer RNA nuclease resistance, the RNA molecules may be modified at the 2' position of the sugar, e.g. amino substitution.

The biopanning protocol will be essentially identical whether the library is based on RNA aptamers or ssDNA aptamers, or whether the library is naive or biased. Basically, the difference will be that ssDNA libraries will not require transcription.

(ii) Biopanning of Phage Display Peptide or Antibody Libraries with Holo-TC

One pmol of phage display library is mixed with 10 μg of holo-TC immobilized on beads and 100 μg of apo-TC in 100 μL PBS-TWEEN® with 1 mg/mL BSA or 3% BLOTTO. (BLOTTO is 5% w/v non-fat powdered milk in 100 mM sodium phosphate, 150 mM sodium chloride, pH 7.4, 0.01% Antifoam A, 0.01% thimerosal). The mixture is incubated at 4° C. overnight and the beads are separated through centrifugation and washed 9 times with 1 mL PBS-TWEEN® and one time with normal saline to remove any buffering capacity. The beads are resuspended in 600 μL of 0.1 M glycine-HCl buffer, pH 2.2 and after 15 min the beads are separated through centrifugation at 3000 g for 3 mm. The supernatant is removed and neutralized with 36 μL of 2M Tris, pH 9.0, and mixed with 400 μL of *Escherichia coli* (e.g. K91-Kan). Plasmids are isolated from single bacterial clones and are screened and sequenced using standard techniques as described in e.g. Sambrook J. et al., supra. The binding and elution reactions are performed at least three times. BSA and BLOTTO are used alternating in the binding reaction to prevent enrichment of phages binding to these proteins.

Example 2

Immobilization of TC Specific Binder on Cellulose Paper

Cellulose paper (e.g. Whatman No. 52) is activated by first swelling it in deionized water for 3 min and then treating it with 3% CNBr (aq). The pH is raised to 10.5 by addition of 1 mM NaOH. After 30 min the paper is washed with 12×500 mL 5 μM NaHCO$_3$, 2×500 mL deionized water, 2×500 mL of each of 25%, 50%, and 75% acetone. Finally it is washed with 4×500 mL acetone and air dried at room temperature.

Covalent coupling of anti-TC antibody is performed by dilution of the antibody to 10 μg/mL in 100 mL 0.1M NaHCO$_3$ and adding 20 g of cut paper. The mixture is stirred gently for 3 h at 4° C., then washed at room temperature for 10 min with 2×100 mL 0.5 mM NaHCO$_3$, for 3 h with 100 mL 50 mM ethanolamine in 0.1 M NaHCO$_3$, for 10 min with 2×100 mL 0.5 mM NaHCO$_3$, for 30 min with 100 mL 0.1 M sodium acetate, pH 4.0, and twice with 50 mM phosphate buffer, pH 7.5, containing 0.15M NaCl, 0.1% TWEEN® 20, and 0.1% gelatin. The antibody loaded paper is stored in a small volume of this buffer.

Sections of the antibody loaded paper are then adhered to a flexible plastic dipstick.

Example 3

Assay

50 μL of human serum is applied to the membrane pad of a dipstick prepared according to Example 2. After 5 min, the dipstick is rinsed with 100 μL of Tris-buffered saline (TBS—100 mM Tris, pH 7.2, 150 mM sodium chloride) and 50 μL of a Detection solution is added and incubated for 5 minutes. The Detection solution contains a non-overlapping, anti-human TC specific monoclonal antibody conjugated to β-galactosidase and a holo-TC sbp according to Example 1 (or a non-overlapping anti-human holo-TC monoclonal antibody) conjugated to chicken alkaline phosphatase. The dipstick is then rinsed with 100 μL, TBS. 50 μL, of a luminescent substrate to alkaline phosphatase in TBS is added (e.g. 0.25 mM CDP-STAR® from Tropix). The dipstick is measured in a luminometer for 1 s to 15 minutes. The dipstick is then rinsed with 100 μL, PBS (phosphate buffered saline), and 50 μL, of a luminescent substrate for β-galactosidase in PBS (e.g. 0.1 mM GALACTON-STAR® from Tropix), and an alkaline phosphatase inhibitor (e.g. 40 μM cyclohexane-trismethylenesulfonate), are added. The dipstick is then read once more in the luminometer. Whereas the first reading gives the holo-TC content on the dipstick, the second reading gives the total TC content. The ratio of the two gives the volume independent value for the cobalamin saturation of TC in the sample.

Example 4

Development of Mouse Monoclonal Antibodies Specific for Human Transcobalamin and Human Holo-Transcobalamin i) Immunization.

BALB/c female mice were immunized i.p. with 20 μg of recombinant human holo-transcobalamin mixed with Adju-Prime Immune modulator (Pierce, Ill., USA), followed by two booster injections of 20 μg at four week intervals.

ii) Fusion.

Four days after the final boost, spleens were removed and splencystes fused to the HAT (Hypoxanthine, Aminopterin, Thymidine; Sigma) sensitive plasmacytoma OUR1 (a subclone of X63-Ag8.653) using PEG (Boehringer Mannheim, Germany). Fusion products were plated over 5×96F trays (Nunc) in the presence of HAT in culture medium (DMEM/Ham's F12 (Invitrogen) plus 10% CPSR3 (Sigma). Fusions were fed after 1 week with culture medium containing HT (Sigma).

iii) Primary Screening.

After two weeks, medium from the hybridomas was screened using a solid phase capture assay. The cell media were mixed with 10 μL of 1% (w/v) suspension of 1 μm magnetizable beads coated with a sheep anti-mouse IgG antibody (Merck-Estapor, France) and kept at ambient temperature for 1 h. The magnetizable beads with bound mouse monoclonal antibodies were isolated by using a magnet, and washed four times with 1 mL phosphate buffer, pH 7.2, 0.15M NaCl and 1 mg/mL bovine serum albumin. Washed beads were resuspended in 100 μL of pooled human serum (Scantibodies, USA) which had been pretreated with 57Co-labeled cobalamin (ICN, USA) to convert apo-transcobalamin in the serum into 57Co-labeled holoTC. The mixtures were kept at ambient temperature for 30 min and beads isolated by using a magnet. The radioactivity associated with the beads was counted in a gamma counter.

iv) Cloning.

Wells positive for anti-transcobalamin antibodies were cloned by limiting dilution over 96wellF trays (Nunc), pre-seeded with Balb/c peritoneal feeder cells (10,000 per well). Positive clones were selected, and recloned until 100% of the subclones were producing specific antibody. Cell stocks were frozen in liquid nitrogen, in CPSR3 (Sigma) containing 10% DMSO (Sigma).

Secondary Screening.

Antibodies from cell media were isolated on magnetizable beads as described above. Ten μL of the antibody coated beads were mixed with serum prelabeled with 57-Co, as described above, in the presence of increasing concentrations of recombinant, human apo-transcobalamin or recombinant, human holo-transcobalamin.

Two anti-transcobalamin antibodies (mAb1 and mAb2) were selected based on their affinity for both apo- and holo-transcobalamin and one monoclonal antibody (mAb3) was selected based on specificity for holo-transcobalamin. The respective clones were expanded in vitro in Tecnomouse, CL1000. Antibodies were purified from cell medium by protein A affinity chromatography. In short, the antibody containing culture supernatant was diluted 1:1 in 0.1M Tris, pH 8.0, containing 1M NaCl (binding buffer) and applied to the protein A column, which had been pre-equilibrated with binding buffer. The protein A column was then extensively washed with 15 column volumes of binding buffer. The antibody was eluted with 0.1M citrate buffer, pH 4.0, neutralized to pH 7.0 with 1M Tris buffer, pH 8, and buffer changed on a Sephadex G-25 column (Pharmacia) to 0.1M phosphate, pH 7.2, containing 0.15M NaCl.

Example 5

Immobilization of TC Specific Monoclonal Antibody mAb1 on Dextran Coated Surface The carboxylated surface of the dextran coated chip (Pharmacia, Sweden) was activated with 0.05M N-hydroxysuccinimide (NHS)/0.2M N-ethyl-N'-[3-(dimethylamino)propyl] carbodiimide hydrochloride (EDC), rinsed with deionized water and coated covalently with mAb1 (from Example 4) at 50 μg/mL in 0.01 HEPES buffer, pH 7.4, containing 0.15M NaCl, 0.003M EDTA, and 0.005% polysorbate (HBS). Unreacted NHS was blocked by 1M ethanolamine and the chip washed extensively with HBS.

Example 6

Binding of Holo-Transcobalamin, mAb2, and mAb3 to Immobilized mAb1

The binding events were followed in real time using surface plasmon resonance and performed on a Biocore instrument (Biacore, Sweden). The amount of free ligand binding to the chip was measured in response units (RU), which reflect both the mass of ligand binding and its affinity for the immobilized target. The chip with immobilized mAb1 (Example 5) was introduced into the instrument, after which was injected 5 μL of 100 nM holo-transcobalamin, 5 μL of 50 μg/mL mAb2, and 5 μL of 50 μg/mL mAb3 successively with washing steps between each. After flowing holo-transcobalamin through the instrument, 565 RU of mAb3 bound to the immobilised mAb1. In the absence of holo-transcobalamin neither mAb2 nor mAb3 bound to the chip with the immobilized mAb1.

The invention claimed is:

1. A volume-independent assay method for the determination of a ratio of holo transcobalamin to total transcobalamin content in a transcobalamin-containing liquid sample, said method comprising:
   (i) providing said liquid sample, in which the quantity of said sample is not precisely determined; contacting said sample with a porous substrate having immobilized thereon in a first region a first transcobalamin-immobilizing antibody, being capable of specific binding to holo transcobalamin, so as to generate a first transcobalamin bound region having holo transcobalamin bound thereto, and in a second region a second transcobalamin-immobilizing antibody being capable of immobilizing apo or apo and holo transcobalamin, so as to generate a second transcobalamin bound region having apo or apo and holo transcobalamin bound thereto;
   (ii) before, during or after step (i) above, contacting transcobalamin of said sample with a reporter-labeled binding partner for transcobalamin, so as to immobilize said reporter-labeled binding partner by binding to said first and second transcobalamin bound regions; and
   (iii) detecting signals from the reporter-labeled binding partner immobilized on the first and second regions and determining the relative levels of holo transcobalamin and total transcobalamin in the sample based on the detected signals;
   wherein the relative level of holo transcobalamin in the sample is determined as the signal from the first region; and
   wherein the relative level of total transcobalamin is determined as the signal from the second region when the second antibody is capable of immobilizing apo and holo transcobalamin; or as the sum of the signals from the first and second regions when the second antibody is capable of immobilizing apo transcobalamin;
   (iv) calculating the ratio of the relative holo transcobalamin level to the relative total transcobalamin level;
   wherein the method is performed without determining absolute amounts of holo transcobalamin and total transcobalamin.

2. The method of claim 1 wherein said first transcobalamin-immobilizing antibody comprises an antibody selected from the group consisting of monoclonal antibodies, antibody fragments, single chain antibodies, antibody fragment dimers, antibody fragment trimers, and antibody fragment tetramers.

3. The method of claim 2 wherein said first transcobalamin-immobilizing antibody comprises a monoclonal antibody.

4. The method of claim 1 wherein said first transcobalamin-immobilizing antibody has a specificity for holo transcobalamin versus apo transcobalamin which is at least 10-fold.

5. The method of claim 4, wherein the signals from the first and second regions are detected simultaneously, and the specificity of the first transcobalamin-immobilizing antibody for holo transcobalamin is at least 100 fold in excess of that for apo transcobalamin.

6. The method of claim 1 wherein said signals are electromagnetic radiation.

7. The method of claim 6 wherein said signals are detected by a digital camera.

8. The method of claim 1 wherein said sample is blood or a blood-derived liquid.

9. The method of claim 1 wherein said substrate is a cellulose sheet.

10. The method of claim 1 wherein said substrate is mounted on a dipstick.

11. The method of claim 1 wherein in step (i) said sample is applied to a first face of said porous substrate and is drawn into said porous substrate by capillary flow promoted by a water absorbent material adjacent to a second face opposed to the first face of said porous substrate.

12. The method of claim 1 wherein said reporter labelled specific binding partner is labelled only by its own mass and is detected by surface plasmon resonance.

13. The method of claim 1 wherein said second transcobalamin-immobilizing antibody comprises an antibody selected from the group consisting of polyclonal antibodies, monoclonal antibodies, antibody fragments, single chain antibodies, antibody fragment dimers, antibody fragment trimers, and antibody fragment tetramers.

14. The method of claim 13 wherein said second transcobalamin-immobilizing antibody comprises a monoclonal antibody.

15. The method of claim 1, wherein the signals from the first and second regions are detected simultaneously.

* * * * *

```
SEQUENCE LISTING

<160> NUMBER OF SEQ ID NOS: 5

<210> SEQ ID NO 1
<211> LENGTH: 71
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(55)
<223> OTHER INFORMATION: n is any base

<400> SEQUENCE: 1
gggaggacga tgcggnnnnn nnnnnnnnnn nnnnnnnnnn nnnnncagac        60
gactcgcccg a                                                  71

<210> SEQ ID NO 2
<211> LENGTH: 32
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<223> OTHER INFORMATION: Primer

<400> SEQUENCE: 2
taatacgact cactataggg aggacgatgc gg                           32

<210> SEQ ID NO 3
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<223> OTHER INFORMATION: Primer
```

```
<400> SEQUENCE: 3
tcgggcgagt cgtctg                                                16

<210> SEQ ID NO 4
<211> LENGTH: 40
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<223> OTHER INFORMATION: Primer

<400> SEQUENCE: 4
ccgaagctta atacgactca ctatagggag gacgatgcgg                      40

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<223> OTHER INFORMATION: Primer

<400> SEQUENCE: 5
gccggatcct cgggcgagtc gtctg                                      25
```